United States Patent
Hwang

(10) Patent No.: US 7,195,924 B2
(45) Date of Patent: Mar. 27, 2007

(54) METHOD FOR IMMOBILIZING A BIOMOLECULE ON A SOLID SUBSTRATE AT A HIGH DENSITY BY USING THE SUBSTRATE HAVING AN ACTIVATED CARBOXYL GROUP ON A SURFACE THEREOF AND MICROARRAY PRODUCED USING THE METHOD

(75) Inventor: Kyu-youn Hwang, Incheon-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/028,822

(22) Filed: Jan. 4, 2005

(65) Prior Publication Data

US 2005/0153350 A1    Jul. 14, 2005

(30) Foreign Application Priority Data

Jan. 12, 2004  (KR) .................... 10-2004-0001963

(51) Int. Cl.
| | | |
|---|---|---|
| G01N 33/551 | (2006.01) | |
| G01N 33/552 | (2006.01) | |
| G01N 33/554 | (2006.01) | |
| G01N 33/20 | (2006.01) | |
| C12Q 1/00 | (2006.01) | |
| C07F 7/04 | (2006.01) | |

(52) U.S. Cl. .................. 436/524; 436/73; 436/527; 436/528; 435/4; 435/970; 530/810; 556/439

(58) Field of Classification Search ............. 436/524, 436/527, 73, 528; 435/4, 970; 530/810; 556/439

See application file for complete search history.

(56) References Cited

U.S. PATENT DOCUMENTS

| | | | |
|---|---|---|---|
| 5,071,746 A | 12/1991 | Wilk et al. | 435/7.94 |
| 5,320,944 A | 6/1994 | Okada et al. | 435/7.94 |
| 5,643,721 A | 7/1997 | Spring et al. | 435/6 |
| 6,413,722 B1 | 7/2002 | Arnold et al. | 435/6 |
| 6,528,264 B1 * | 3/2003 | Pal et al. | 435/6 |
| 6,989,267 B2 * | 1/2006 | Kim et al. | 435/287.2 |

OTHER PUBLICATIONS

European Search Report; Application No. 05000285.6-2402-; Date of Completion: Apr. 13, 2005.

* cited by examiner

Primary Examiner—Long V. Le
Assistant Examiner—Shafiqul Haq
(74) Attorney, Agent, or Firm—Cantor Colburn LLP

(57) ABSTRACT

Provided is a method for immobilizing a biomolecule on a solid substrate. The method includes coating the solid substrate with silane anhydride to introduce an anhydride functional group onto a surface of the solid substrate; obtaining a carboxyl group from the anhydride functional group by hydrolysis; reacting the carboxyl group with carbodiimide and succinimide to activate the carboxyl group; and contacting the biomolecule with the solid substrate having the activated carboxyl group on its surface to immobilize the biomolecule on the solid substrate.

14 Claims, 5 Drawing Sheets

METHOD FOR IMMOBILIZING A BIOMOLECULE ON A SOLID SUBSTRATE AT A HIGH DENSITY BY USING THE SUBSTRATE HAVING AN ACTIVATED CARBOXYL GROUP ON A SURFACE THEREOF AND MICROARRAY PRODUCED USING THE METHOD

BACKGROUND OF THE INVENTION

This application claims the benefit of Korean Patent Application No. 10-2004-0001963, filed on Jan. 12, 2004, in the Korean Intellectual Property Office, the disclosure of which is incorporated herein in its entirety by reference.

1. Field of the Invention

The present invention relates to a method for immobilizing a biomolecule on a microarray substrate and a biomolecule microarray produced using the method.

2. Description of the Related Art

The term "microarray" refers to a substrate having specific molecules immobilized on predetermined regions at a high density. Examples of the microarray include, for example, a polynucleotide microarray and a protein microarray. Such microarrays are well known in the art, and examples are disclosed in U.S. Pat. Nos. 5,445,934 and 5,744,305. Generally, microarrays are produced by using photolithographic technology. In the photolithographic method, a predetermined region of a substrate coated with a monomer having a removable protective group is exposed to an energy source to remove the protective group from the monomer, and then a second monomer having a removable protective group is coupled to the monomer. The process of exposure to an energy source, removal of the protective group, and coupling of a monomer is repeated to produce a desired polynucleotide on the substrate. Alternatively, microarrays are produced using a method in which a previously synthesized polynucleotide is immobilized at a predetermined location on a substrate, such as a spotting method, a piezoelectric printing method, for example, using an inkjet printer, and a micro-pipetting method, etc. This approach permits biomolecules to be freely arranged, and thus is widely used.

In general, it is difficult to immobilize biomolecules on a surface of a substrate, such as glass or plastics. In conventional methods, in order to immobilize a previously synthesized biomolecule to a solid substrate, the substrate surface was treated to have specific functional groups. Examples of the functional groups include an amino group, an aldehyde group, an epoxide group, and an ester group.

Methods including coating a solid substrate with functional groups and then immobilizing activated biomolecules thereon have been proposed. For example, U.S. Pat. No. 5,350,800 discloses a method including activating a carboxyl group of a carboxyl group containing protein, for example, heparin or laminin using carbodiimide and reacting the resultant product with a solid substrate coated with an amine group to immobilize the product. U.S. Pat. No. 5,760,130 discloses a method including immobilizing a polynucleotide activated with phosphorimidazolide on a glass substrate coated with an amino group. However, in the conventional methods, since the substrate coated with an amino group is used, activation of the biomolecule is required.

U.S. Pat. No. 5,760,130 discloses a method for immobilizing a polynucleotide on a plastic plate which has a carboxyl group. In this method, for example, "Sumilon" MS-3796F and MS-3696F (available from Sumitomo Bakeliet), which have both a carboxyl group and an amino group, can be used. However, in this method, since the plastic plate has a carboxyl group, there is a problem that a density of carboxyl group is too low. Further, this method disclosed in U.S. Pat. No. 5,760,130 is intended to synthesize cDNAs using a support having polynucleotides immobilized thereon. Thus, it is not required to measure fluorescence intensity for analysis of a target biomolecule as in a microarray. The patent does not list a need for introducing the carboxyl groups at a high density. Thus, the present inventors conducted vigorous research to increase fluorescent signal intensity obtained from an analysis of a target biomolecule by immobilizing the biomolecule on a microarray substrate at a high density, and discovered a method for immobilizing a biomolecule on a substrate at a high density by using a carboxylic anhydride.

SUMMARY OF THE INVENTION

The present invention provides a method for immobilizing a biomolecule on a substrate at a high density by using the substrate having an activated carboxyl group on its surface.

The present invention also provides a microarray produced using the above method.

According to an aspect of the present invention, there is provided a method for immobilizing a biomolecule on a solid substrate, comprising:

coating the solid substrate with silane anhydride to introduce an anhydride functional group onto a surface of the solid substrate;

exposing a carboxyl group from the anhydride functional group by hydrolysis;

reacting the carboxyl group with carbodiimide and succinimide to activate the carboxyl group; and contacting the biomolecule with the solid substrate having the activated carboxyl group on its surface to immobilize the biomolecule on the solid substrate.

According to another aspect of the present invention, there is provided method for immobilizing a biomolecule on a solid substrate, comprising:

coating the solid substrate with aminosilane to introduce an amino functional group onto a surface of the solid substrate;

reacting the amino functional group with tetracarboxylic dianhydride to introduce an anhydride functional group into the surface of the solid substrate;

exposing a carboxyl group from the anhydride functional group by hydrolysis;

reacting the carboxyl group with carbodiimide and succinimide to activate the carboxyl group; and contacting the biomolecule with the solid substrate having the activated carboxyl group on its surface to immobilize the biomolecule on the solid substrate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
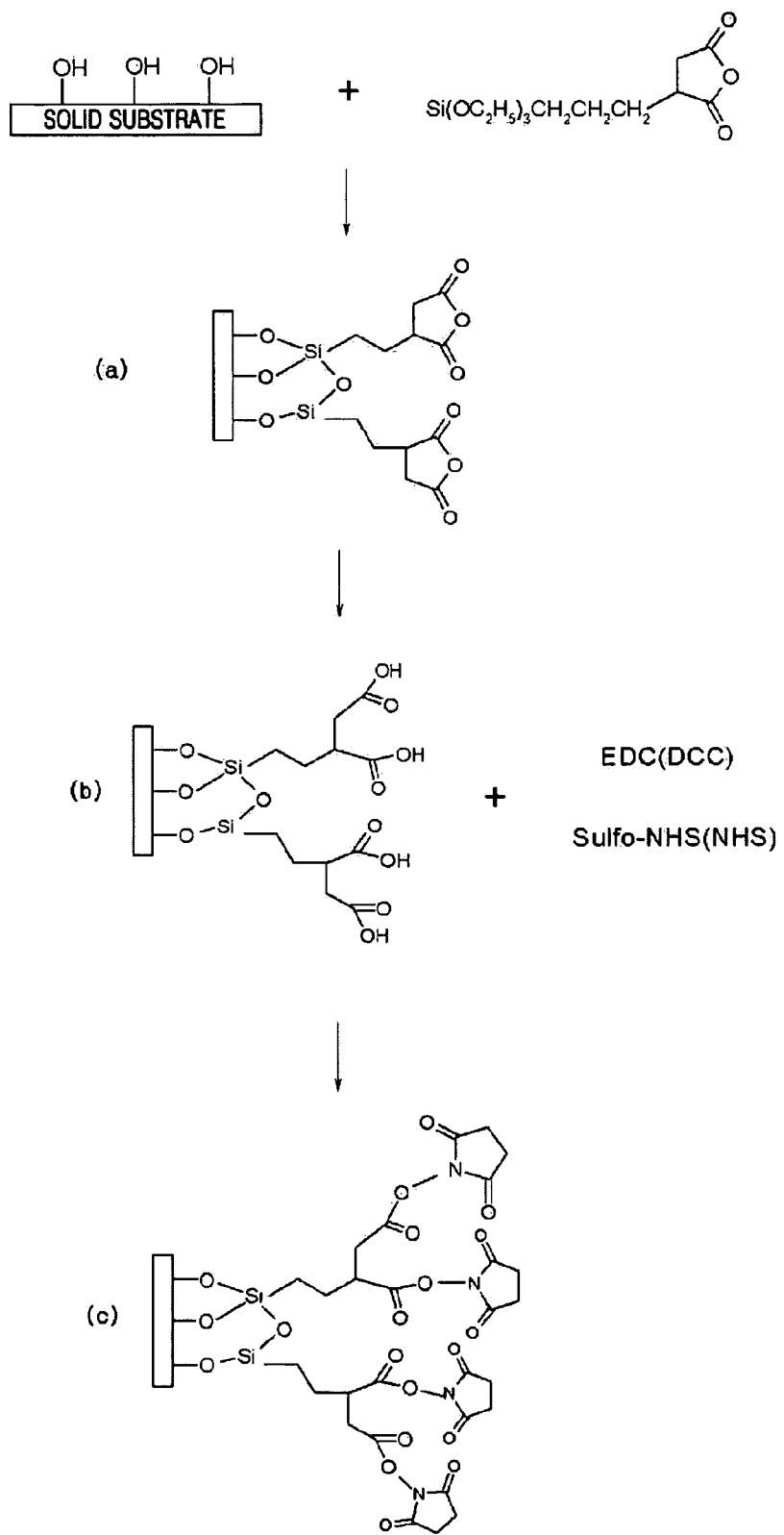
FIG. 1 is a view illustrating a method of producing a microarray substrate having an activated carboxyl group on its surface according to an embodiment of the present invention.

According to an embodiment of the present invention, there is provided a method for immobilizing a biomolecule on a solid substrate, comprising:

coating the solid substrate with silane anhydride to introduce an anhydride functional group onto a surface of the solid substrate;

exposing a carboxyl group from the anhydride functional group by hydrolysis;

reacting the carboxyl group with carbodiimide and succinimide to activate the carboxyl group; and contacting the biomolecule with the solid substrate having the activated carboxyl group on its surface to immobilize the biomolecule on the solid substrate.

In the method according to the present embodiment, the solid substrate is not specifically limited and may be transparent or opaque. The solid substrate may be a material which is environment-friendly or resistant to chemicals. Examples of the solid substrate include glass, silicon wafer, polyethylene, polypropylene, polycarbonate, polyester, polyacrylate, and polyurethane.

In the method according to the present embodiment, the silane anhydride may be a compound represented by formula I:

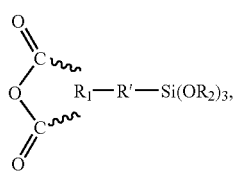

wherein $R_1$ is an alkylene group, an arylene group or an alkylarylene group, preferably a $C_1$–$C_{20}$ straight or branched chain alkylene group, and more preferably a methyl, ethyl, propyl, or butyl group, R' is a substituted or unsubstituted $C_1$–$C_{20}$ alkylene group, a $C_1$–$C_{20}$ arylene group, a $C_1$–$C_{20}$ arylenealkyl group or a $C_1$–$C_{20}$ alkylenearylene group, $R_2$ is a $C_1$–$C_{20}$ alkyl group, an aryl group, an arylenealkyl group, an alkylenearyl group or a hydrogen atom, and the respective $R_2$ groups may be identical to or different from each other. More preferably, the silane anhydride may be 3-(triethoxysilyl)propylsuccinic anhydride, which is available, for example, from Gelest, Inc.

In the method according to the present embodiment, the solid substrate may be coated with a solution containing 0.01 to 90% by weight of the silane anhydride.

Moreover, in the coating the solid substrate with a silane anhydride, the solid substrate may be coated with a silane anhydride solution further comprising a silane compound represented by any one of formulae II and III:

wherein $R_3$ is a $C_1$–$C_{20}$ alkoxy group, a hydroxy group, or a halogen, $R_4$ is a $C_1$–$C_{20}$ straight or branched chain alkyl group, an aryl group, an arylenealkyl group, or an alkylenearyl group, or a fluorinated hydrocarbon functional group, including $CF_3$, and n is an integer of 1 to 15,

wherein, $R_5$ is a $C_1$–$C_{20}$ straight or branched chain alkyl group, an aryl group, an arylenealkyl group or an alkylenearyl group, or a hydrogen atom.

The amount of the silane compound represented by any one of formulae II and III may be 0 to 0.01 parts by weight based on 100 parts by weight of the silane anhydride.

The solution for coating is prepared by diluting the compound represented by formula I in a suitable solvent or by mixing the compound represented by formula I with the silane compound represented by any one of formulae II and III. A weight ratio of the silane anhydride of formula I to the silane compound represented by any one of formulae II and III may be 0.01:99.99 to 100:0. The synthesized silane oligomer may be contained in an amount of 0.01 to 90% by weight in the coating solution. Examples of the solvent which can be used include an alcohol solvent, such as methanol, ethanol, propanol, and butanol, and methyl ethyl ketone, dimethyl formamide, methylpyrrolidone(N-methylpyrrolidone), and mixtures thereof.

In the method according to the present embodiment, a method of coating the silane anhydride is well known in the art and may be performed using a method selected from the group consisting of dip coating (self-assembly molecular coating), spin coating, spraying, and chemical vapor deposition. Dip coating can be performed for 1 minute or more. Spin coating can be performed at speeds of 300 to 2,500 rpm. The coating layer of the anhydride formed with this method may be cured at about 100 to 300° C. to form a three-dimensional network structure.

In the method according to the present embodiment, hydrolysis of the anhydride may be performed in an aqueous solution at 20 to 100° C. The hydrolysis may be carried out by treating the anhydride with an acidic or neutral solution for at least one minute at the temperature of 20 to 100° C., and then drying the resultant product under a nitrogen atmosphere. Due to the hydrolysis, two carboxyl groups are induced from one anhydride, and thus a substrate can be produced having carboxyl groups thereon at a high density.

Thus, activated carboxyl groups can be formed on the substrate at a high density, and then, biomolecules can be chemically bound to the activated carboxyl groups. For example, in the conventional method, succinic anhydride is reacted with a substrate having an amino group on its surface to form a carboxyl group. Meanwhile, in the method according to the present embodiment, the substrate can have a carboxyl group at a density two-fold higher than the conventional substrate having an amino group on its surface. When using a microarray produced using the substrate according to an embodiment of the present invention in an analysis, fluorescence intensity detected can be increased.

In the method according to the present embodiment, the carbodiimide may be represented by formula IV:

wherein $R_6$ is an alkyl group or a cycloalkyl group, and $R_7$ is an alkylamino group or an acycloalkylamino group.

In the method according to the present embodiment, the carbodiimide may be 1-ethyl-3-(3-dimethyl-aminopropyl) carbodiimide hydrochloride (EDC) or N,N'-dicyclohexyl carbodiimide (DCC). The succinimide may be N-hydroxysuccinimide or N-hydroxysulfosuccinimide. The carbodiimide or the succinimide may be reacted in a suitable solvent at 20 to 200 mM. The reaction time may be at least 30 minutes, but is not specifically limited. The carbodiimide or the succinimide such as N-hydroxysuccinimide is commercially available from Aldrich Chemical Co., Inc.

It is assumed that the reaction of a carboxyl group with carbodiimide and succinimide will occur via the following mechanism, but not be limited thereto. First, a carboxyl group on a substrate surface and carbodiimide form an unstable intermediate that can react with an amino group, i.e., O-acylisourea ester bond. Then, the resultant bond reacts with N-hydroxysuccinimide (NHS) or water-soluble N-hydroxysulfosuccinimide to form a more stable succinimidyl ester, thus providing the substrate having an activated carboxyl group on its surface.

In the method according to the present embodiment, the biomolecule to be immobilized may be any one having a functional group capable of chemically bonding to the activated ester group, for example, an amino group. The biomolecule may be DNA, RNA, PNA, or a protein.

When reacting a biomolecule having a reactive functional group, such as an amino group with a substrate having an activated carboxyl group on its surface produced according to the present embodiment, the biomolecule acts on an ester bond of the activated carboxyl group to form an amide bond, and thus the biomolecule is immobilized on the substrate. Such an immobilization method has an advantage in that the number of non-specific bonds between target materials and a substrate which can occur during hybridization can be remarkably reduced.

FIG. 1 is a view illustrating a method of producing a microarray substrate having an activated carboxyl group on its surface according to an embodiment of the present invention. First, a solid substrate is coated with a silane anhydride, i.e., 3-(triethoxysilyl)propylsuccinic anhydride (TSA) (a). Next, hydrolysis reaction is performed to obtain a substrate having a carboxyl group on its surface (b) and the obtained substrate is reacted with carbodiimide, such as 1-ethyl-3-(3-dimethyl-aminopropyl) carbodiimide hydrochloride (EDC) and N,N'-dicyclohexyl carbodiimide (DCC), and succinimide, such as N-hydroxysuccinimide (NHS) and N-hydroxysulfosuccinimide (Sulfo-NHS) to obtain the substrate having an activated carboxyl group on its surface (c).

According to another embodiment of the present invention, there is provided a biomolecule microarray which is produced using the above method of immobilizing a biomolecule on a surface of a solid substrate. In this biomolecule microarray, spot regions on which the biomolecules are immobilized are arranged in an array form, as in the conventional microarray.

Methods for immobilizing a biomolecule on a substrate are well known in the art. Examples include a spotting method which is contact-type, a piezoelectric printing method, for example, using an inkjet printer, and a micropipetting method, etc.

According to still another embodiment of the present invention, there is a method for immobilizing a biomolecule on a solid substrate, comprising:

coating the solid substrate with aminosilane to introduce an amino functional group onto a surface of the solid substrate;

reacting the amino functional group with tetracarboxylic dianhydride to introduce an anhydride functional group into the surface of the solid substrate;

exposing a carboxyl group from the anhydride functional group by hydrolysis;

reacting the carboxyl group with carbodiimide and succinimide to activate the carboxyl group; and contacting the biomolecule with the solid substrate having the activated carboxyl group on its surface to immobilize the biomolecule on the solid substrate.

In the method according to the present embodiment, the solid substrate may be coated with a solution containing 0.01 to 90% by weight of the aminosilane compound.

In the method according to the present embodiment, the aminosilane is a primary aminosilane represented by formula V or a secondary aminosilane represented by formula VI:

wherein $R_8$ is an alkylene group, an arylene group, an arylenealkylene group, alkylenearylene group, ether, ester, or an imine containing group, and $R_9$ is a $C_1$–$C_{20}$ alkyl group, an aryl group, an arylenealkyl group, or an alkylenearyl group, or a hydrogen atom.

$R_8$ and $R_9$ are preferably an alkyl group, and more preferably a methyl, ethyl, propyl, or butyl group. Examples of the aminosilane include 3-aminopropyltrimethoxysilane, 3-aminopropyltriethoxysilane, 2-aminoundecyltrimethoxysilane, aminophenyltrimethoxysilane, bis(trimethoxysilylpropyl)amine, and N-(2-aminoethylaminopropyl)triethoxysilane.

In the coating the solid substrate with aminosilane, first, at least one compound represented by formula V or VI is mixed to obtain a mixture of the aminosilane compounds, to which water and an alcohol solvent, such as ethanol and methanol, are added. Next, the resulting solution is stirred and the silane compounds are subject to a condensation reaction to obtain an oligomer hydrate in the solution. A substrate is coated with the aminosilane compound(s) and baked at about 200 to 300° C. to form a layer having a three-dimensional network structure.

In addition, in the coating the solid substrate with aminosilane, the solid substrate may be coated with an aminosilane solution further comprising a silane compound represented by any one of formulae II and III:

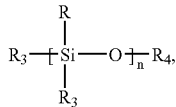
(II)

wherein

R$_3$ is a C$_1$–C$_{20}$ alkoxy group, a hydroxy group, or a halogen, R$_4$ is a C$_1$–C$_{20}$ straight or branched chain alkyl group, an aryl group, an arylenealkyl group, or an alkylenearyl group, or a fluorinated hydrocarbon functional group, including CF$_3$, and n is an integer of 1 to 15, $$Si(OR_5)_4 \quad (III),$$

wherein,

R$_5$ is a C$_1$–C$_{20}$ straight or branched chain alkyl group, an aryl group, an arylenealkyl group or an alkylenearyl group, or a hydrogen atom.

As silane compound represented by formulae II or III, a mixture comprised of only a hydrophobic silane compound for controlling hydrophobicity of the amine layer or comprised of only a silane alkoxide for increasing bonding strength to a substrate surface can be used.

The amount of the silane compound represented by formula II or III may be 0.0001 to 0.01 parts by weight based on 100 parts by weight of the aminosilane.

In the method according to the present embodiment, a method of coating the aminosilane is well known in the art and may be performed using a method selected from the group consisting of dip coating (self-assembly molecular coating), spin coating, spraying, and chemical vapor deposition.

In the method according to the present embodiment, the tetracarboxylic dianhydride may be represented by formula VII:

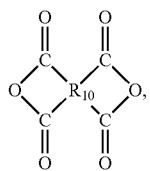
(VII)

wherein

R$_{10}$ is a quaternary organic group, such as a quaternary carboncyclic aromatic, heterocyclic, alicyclic, or aliphatic group.

The tetracarboxylic dianhydride may be selected from the group consisting of pyromellitic dianhydride, 3,3',4,4'-biphenyltetracarboxylic dianhydride, 2,2',3,3'-biphenyltetracarboxylic dianhydride, 2,3,3',4'-biphenyltetracarboxylic dianhydride, 1,2,4,5-benzenetetracarboxylic dianhydride, 3,3',4,4'-benzophenonetetracarboxylic dianhydride, 2,2',3,3'-benzophenonetetracarboxylic dianhydride, 2,3,3',4'-benzophenonetetracarboxylic dianhydride, bis(3,4-dicarboxylphenyl) ether dianhydride, bis(3,4-dicarboxylphenyl) sulfone dianhydride, 1,4,5,8-naphthalenetetracarboxylic dianhydride, 1,2,5,6-naphthalenetetracarboxylic dianhydride, 2,3,6,7-naphthalenetetracarboxylic dianhydride, 2,2-bis(3,4-dicarboxylphenyl)-hexafluoropropane dianhydride, cyclobutanetetracarboxylic dianhydride, methylcyclobutanetetracarboxylic dianhydride, and 1,2,3,4-tetracarboxybutane dianhydride.

In the method according to the present embodiment, the tetracarboxylic dianhydride may be reacted at a concentration of 0.02 to 90% by weight. The tetracarboxylic dianhydride may be reacted in a dissolved state in at least one solvent selected from the group consisting of acetone, methyl ethyl ketone, dimethyl formamide, and N-methylpyrrolidone.

The reaction between the amino functional group on the substrate surface with tetracarboxylic dianhydride may be performed, for example, by coating the tetracarboxylic dianhydride on the amino substrate by dip coating (self-assembly molecular coating) to form a single layer, and then reacting the tetracarboxylic dianhydride with the amino group for at least 10 minutes. The introduction of such dianhydride may be attained through a nueclophilic substitution reaction with the amino group. After the reaction is completed, the tetracarboxylic dianhydride adsorbed on the substrate may be washed away with the solvent for the reaction, and then dried under a nitrogen atmosphere. Further, the remaining washing solvent may be removed by drying in a nitrogen oven.

In the method according to the present embodiment, the hydrolysis of the anhydride may be performed in an aqueous solution at 20 to 100° C. The hydrolysis may be carried out by treating the anhydride with an acidic or neutral solution for at least one minute at the temperature of 20 to 100° C., and then drying the resultant product under nitrogen atmosphere. Due to the hydrolysis, two carboxyl groups are induced from one anhydride, and thus it is possible to produce a substrate having carboxyl groups thereon at a high density. Thus, activated carboxyl groups can be formed at high density on the substrate, and then, biomolecules can be bonded to the activated carboxyl groups. For example, in the conventional method, succinic anhydride is reacted with a substrate having an amino group on its surface to form a carboxyl group. Meanwhile, in the method according to the present embodiment, the substrate can have a carboxyl group at a density two times higher than the conventional substrate having an amino group on its surface. When using a microarray produced using the substrate according to an embodiment of the present invention in an analysis, a higher fluorescence intensity can be detected.

In the method according to the present embodiment, the carbodiimide may be represented by formula IV:

$$R_6N{=}C{=}NR_7 \quad (IV),$$

wherein

R$_6$ is an alkyl group or a cycloalkyl group, and R$_7$ is an alkylamino group or an acycloalkylamino group.

The carbodiimide may be 1-ethyl-3-(3-dimethyl-aminopropyl) carbodiimide hydrochloride (EDC) or N,N'-dicyclohexyl carbodiimide (DCC).

In the method according to the present embodiment, the succinimide may be N-hydroxysuccinimide or N-hydroxysulfosuccinimide.

In the method according to the present embodiment, the carbodiimide or the succinimide may be reacted at 20 to 200 mM.

In the method according to the present embodiment, the biomolecule to be immobilized may be any one having a functional group capable of attaching to the activated ester group, for example, an amino group. The biomolecule may be DNA, RNA, PNA, or a protein.

Figure 2:
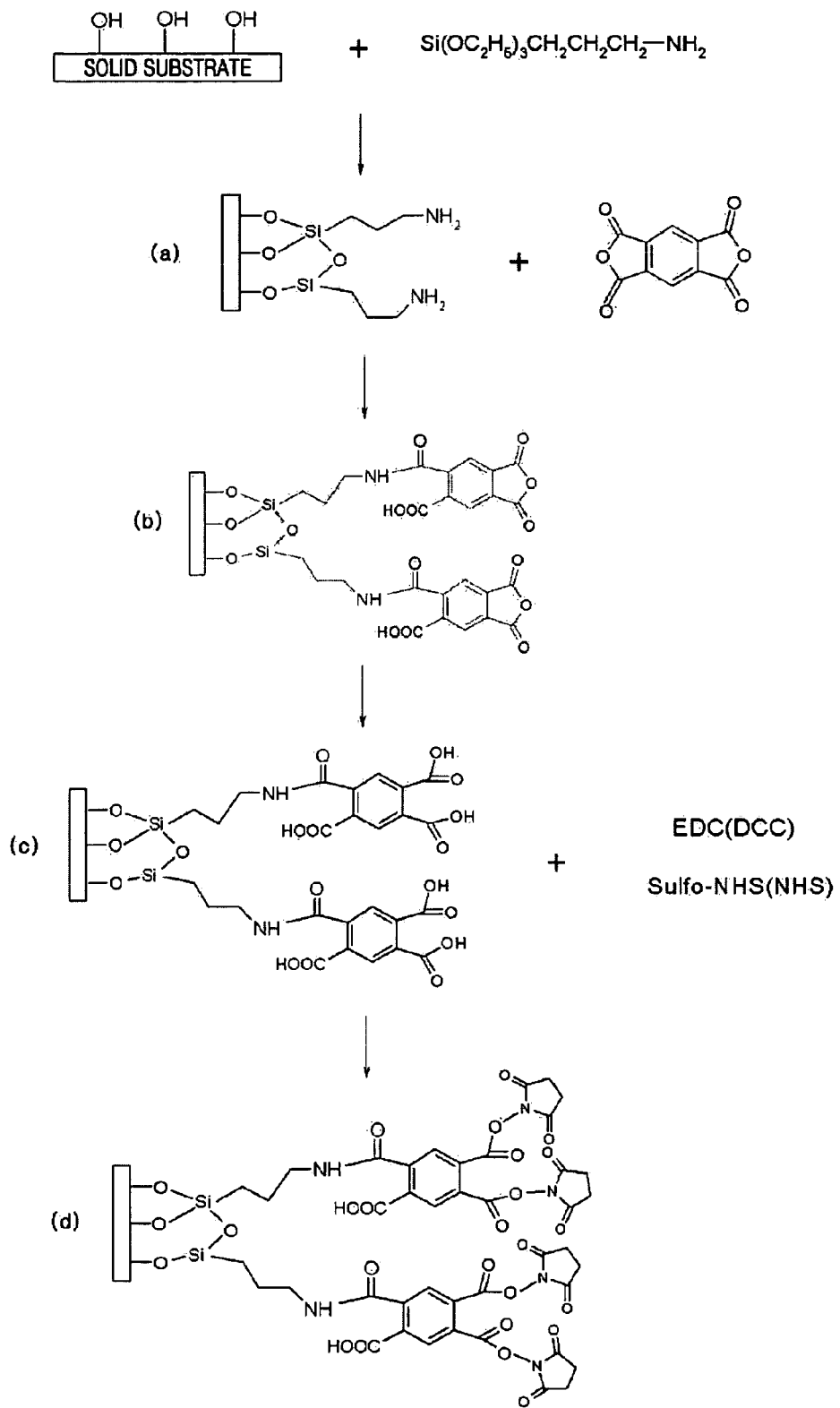
FIG. 2 is a scheme illustrating a method of producing a microarray substrate having an activated carboxyl group on its surface according to an embodiment of the present invention.

FIG. 2 is a scheme illustrating a method of producing a microarray substrate having an activated carboxyl group on its surface according to an embodiment of the present invention. First, a substrate is coated with an aminosilane, such as ɤ-aminopropyltriethoxysilane (GAPS) to obtain the substrate having an amino group on its surface (a). Then, the obtained substrate is reacted with a tetracarboxylic dianhydride, such as 1,2,4,5-benzenetetracarboxylic dianhydride to introduce the dianhydride into the substrate (b). Next, a hydrolysis reaction is performed to obtain the substrate having a carboxyl group on its surface (c) and the obtained substrate is reacted with carbodiimide, such as 1-ethyl-3-(3-dimethyl-aminopropyl) carbodiimide hydrochloride (EDC) and N,N'-dicyclohexyl carbodiimide (DCC), and succinimide, such as N-hydroxysuccinimide (NHS) and N-hydroxysulfosuccinimide (Sulfo-NHS) to obtain the substrate having an activated carboxyl group on its surface (d).

According to still another embodiment of the present invention, there is provided a biomolecule microarray produced using the above method of immobilizing a biomolecule on a surface of a solid substrate.

Methods for immobilizing a biomolecule on a substrate are well known in the art. Examples include a spotting method which is contact-type, a piezoelectric printing method, for example, using an inkjet printer, and a micropipetting method, etc.

Hereinafter, the present invention will be described in more detail with reference to the following examples. However, these examples are given for the purpose of illustration and are not intended to limit the scope of the invention.

EXAMPLE

Example 1

Coating of a Nucleic Acid on a Substrate Having an Activated Carboxyl Group on its Surface and a Substrate Coated with Aminosilane (1) Production of a Substrate Coated with Aminosilane ɤ-aminopropyltriethoxysilane (GAPS) was dissolved in ethanol to obtain a 0.002 M GAPS solution. The obtained solution was coated on a washed glass substrate in the form of slide by dip coating, and then treated at 120° C. for 1 hour to produce a substrate coated with aminosilane.

(2) Production of a Substrate Having an Activated Carboxyl Group on its Surface 3-(triethoxysilyl)propylsuccinic anhydride (TSA) was dissolved in ethanol so that a 0.002 M TSA solution was obtained. The obtained solution was coated on a washed glass substrate in the form of slide by dip coating, and then treated at 120° C. for 1 hour to produce a substrate coated with silane anhydride.

The glass substrate coated with silane anhydride (TSA) was washed in a weak acidic water for 3 minutes to obtain a carboxyl group from the silane anhydride by hydrolysis. Then, the glass substrate having a carboxyl group on its surface obtained was reacted for 1 hour in a DMF solution containing N-hydroxysuccinimide (NHS) and N,N'-dicyclohexyl carbodiimide (DCC) at 100 mM, respectively, to produce a microarray substrate having an activated carboxyl group on its surface. Thereafter, the resultant glass substrate was washed with ethanol and stored in a nitrogen container.

(3) Immobilization of Nucleic Acid and Hybridization Test

An oligonucleotide probe having a nucleotide sequence of SEQ ID No: 1 was mixed with DMSO and spotted using a spotter on the substrate having an activated carboxyl group on its surface and the substrate coated with aminosilane, respectively, obtained from the above process. Immobilization was performed at 37° C., 100% RH for 1 hour, and then post-washing treatment was performed to produce microarrays having the probe immobilized thereon.

Figure 3A:
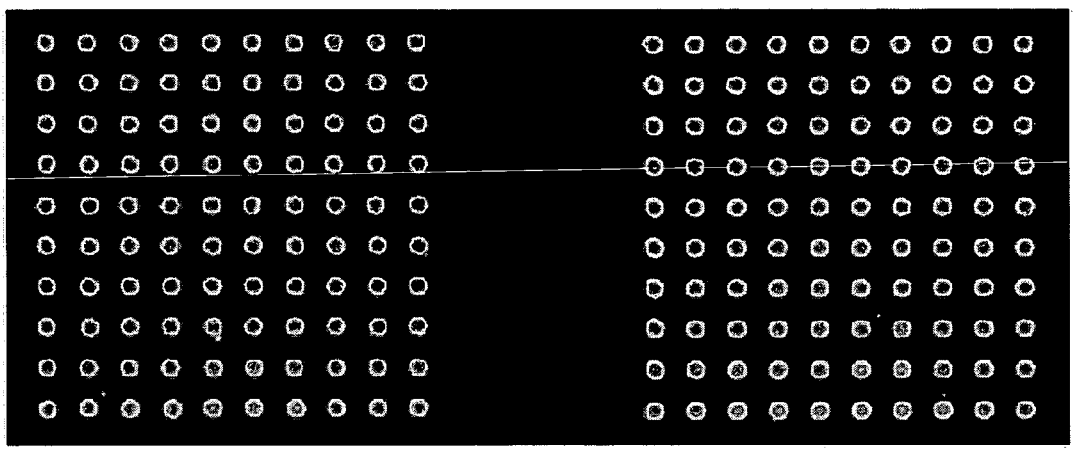
FIGS. 3A and 3B are views illustrating the results of measurements of fluorescence intensities for a microarray in which a nucleic acid probe was immobilized on a substrate which was produced using the method according to an exemplary embodiment of the present invention, and then hybridized with a target nucleic acid and for a microarray in which a nucleic acid probe was immobilized on a conventional substrate, and then hybridized with a target nucleic acid.
Figure 3B:
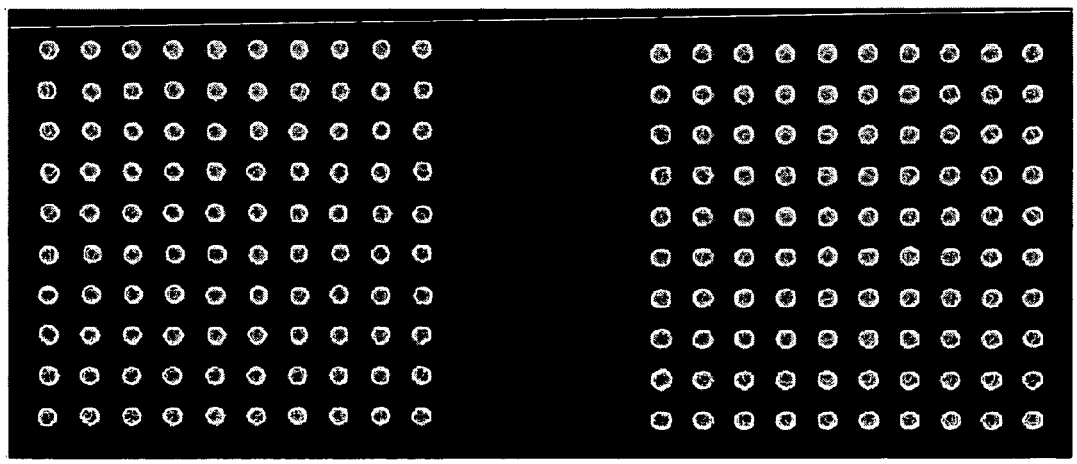
Figure 4A:
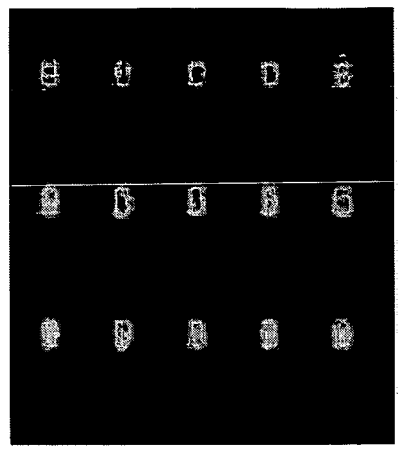
FIGS. 4A through 4D are views illustrating the results of measurements of fluorescence intensities for microarrays in which a nucleic acid probe was immobilized on a substrate produced using the method according to another exemplary embodiment of the present invention, and then hybridized with a target nucleic acid and for microarrays in which a nucleic acid probe was immobilized on a conventional substrate, and then hybridized with a target nucleic acid.
Figure 4B:
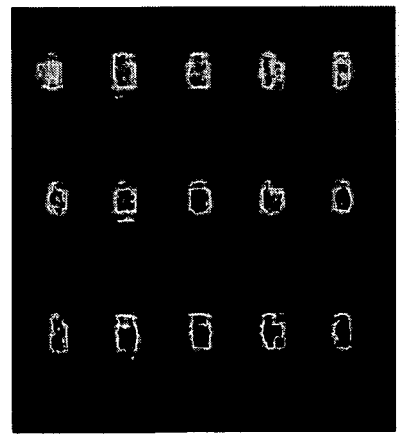
Figure 4C:
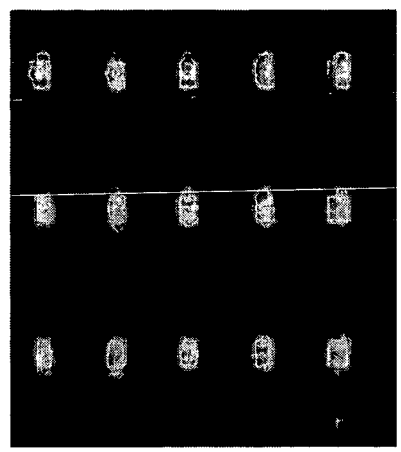
Figure 4D:
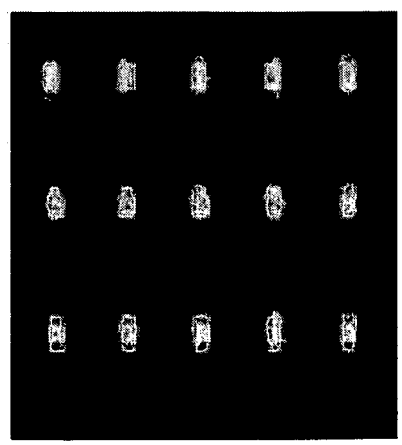

For the respective produced microarrays, a target nucleic acid having a nucleotide sequence complementary to the above probe of SEQ ID No: 1 was hybridized with the above probe. In the hybridization, the target nucleic acid was dissolved in 0.1% SSPET (a saline sodium phosphate EDTA buffer containing 0.1% Triton X-100) and reacted with each microarray at 37° C. for 14 hours. After the reaction, each microarray was washed with 6×SSPET and 3×SSPET for 5 minutes, respectively, and then dried in nitrogen. The dried microarrays were scanned using GenePix 4000B scanner™ (Axon). The results are shown in FIGS. 3A and 3B. In the hybridization, the substrate coated with aminosilane, i.e., amino substrate, was subject to a succinic anhydride/NMP blocking process.

As illustrated from FIGS. 3A and 3B, for a microarray using the substrate having an activated carboxyl group on its surface which was produced using the method according to an embodiment of the present invention, a higher fluorescence intensity and better spot morphology were attained without a need for the blocking process during hybridization. FIG. 3A illustrates the results of the TSA substrate and FIG. 3B illustrates the results of the GAPS substrate, with each left side designating the results for a probe concentration of 100 μM and each right side designating the results for a probe concentration of 25 μM. The results of the measurement of fluorescence intensity illustrated in FIGS. 3A and 3B are shown as numerical values in Table 1.

TABLE 1

| DNA concentration (μM) | TSA | GAPS |
|---|---|---|
| 100 | 17,000 | 12,000 |
| 25 | 14,000 | 11,000 |

Example 2

Coating of a Nucleic Acid on a Substrate Having an Activated Carboxyl Group on its Surface, an Amino Substrate, and a Substrate Having an Activated Carboxyl Group on an Amine Layer (1) Production of a Substrate Having an Activated Carboxyl Group on its Surface 3-(triethoxysilyl)propylsuccinic an hydride (TSA) and 1,2-bis(triethoxysilyl)ethane were dissolved in ethanol so that each concentration of TSA and 1,2-bis(triethoxysilyl) ethane in a solution was 0.002 M. The obtained solution was coated on a washed glass substrate in the form of slide by dip coating, and then treated at 120° C. for 1 hour to produce a substrate coated with silane anhydride.

The glass substrate coated with the above anhydride was washed in a weak acidic water for 3 minutes to obtain a carboxyl group from the silane anhydride by hydrolysis. Then, the glass substrate having a carboxyl group on its surface obtained was reacted for 1 hour in a DMF solution containing N-hydroxysuccinimide (NHS) and N,N'-dicyclohexyl carbodiimide (DCC) at 100 mM, respectively. After the reaction, the resultant glass substrate was washed with ethanol and stored in a nitrogen container. Hereinafter, the obtained substrate was designated as "TSA substrate".

(2) Production of a Substrate Coated with Aminosilane 3-aminopropyltrimethoxysilane and 1,2-bis(triethoxysilyl)ethane were dissolved by stirring in ethanol so that each concentration of 3-aminopropyltrimethoxysilane and 1,2-bis(triethoxysilyl)ethane in a solution was 0.002 M. The obtained solution was coated on a washed glass substrate in the form of slide by dip coating, and then treated at 120° C. for 1 hour to produce a substrate coated with aminosilane. Hereinafter, the obtained substrate was designated as "amino substrate".

(3) Production of a Substrate Having an Activated Carboxyl Group on an Amine Layer The above amino substrate was dipped in a solution containing succinic anhydride or 1,2,4,5-benzenetetracarboxylic dianhydride in DMF in a concentration of 0.01 M, and reacted for 1 hour. After the reaction, each of the resultant substrates was washed with ethanol and dried in a nitrogen container. Then, each of the substrates was washed in a weak acidic water for 3 minutes to obtain a carboxyl group from the anhydride by hydrolysis. Then, the glass substrate having a carboxyl group on its surface obtained was reacted for 1 hour in a DMF solution containing N-hydroxysuccinimide (NHS) and N,N'-dicyclohexyl carbodiimide (DCC) at 100 mM, respectively, to activate the carboxyl group. Once the reaction was completed, the resultant glass substrates were washed with ethanol and stored in a nitrogen container. Hereinafter, the obtained substrates were designated as "SA (succinic anhydride) substrate" and "BD (1,2,4,5-benzenetetracarboxylic dianhydride) substrate", respectivley.

(4) Immobilization of Nucleic Acid and Hybridization Test

An oligonucleotide probe having a nucleotide sequence of SEQ ID No: 1 was mixed with DMSO and spotted using a spotter on each of the substrates obtained above. Immobilization was performed at 37° C., 100% RH for 1 hour, and then a post-washing treatment was performed to produce each microarray having the probe immobilized thereon.

For the respective produced microarrays, a target nucleic acid having a nucleotide sequence complementary to the above probe of SEQ ID No: 1 was hybridized with the above probe. In the hybridization, the target nucleic acid was dissolved in 0.1% SSPET (a saline sodium phosphate EDTA buffer containing 0.1% Triton X-100) and reacted with each microarray at 37° C. for 14 hours. After the reaction, each microarray was washed with 6×SSPET and 3×SSPET for 5 minutes, respectively, and then dried in nitrogen. The dried microarrays were scanned using GenePix 4000B scanner™ (Axon). The results are shown in Table 2 and FIG. 4. In the hybridization, the amino substrate was subject to a succinic anhydride/NMP blocking process.

TABLE 2

|  | Substrate | | | |
| --- | --- | --- | --- | --- |
| Substrate | TSA | BD | SA | Amino substrate |
| Fluorescence intensity | 9588 | 9612 | 4811 | 5294 |
| Succinic anhydride/NMP blocking process | x | X | x | o |

As illustrated in Table 2, for microarrays produced using the method according to an embodiment of the present invention, spots exhibited better characteristics, i.e., higher fluorescence intensity and did not require the blocking process after the immobilization of probe oligonucleotide. FIGS. 4A through 4D include views illustrating the results of hybridization for the microarrays designated as a TSA substrate, BD substrate, SA substrate, and amino substrate, respectively. The fluorescence intensities of the spots are regarded to be stronger toward red color and weaker toward blue color.

When using a method for immobilizing a biomolecule on a solid substrate according to an embodiment of the present invention, two carboxyl groups are induced from one anhydride, and thus, a biomolecule may be immobilized on the solid substrate at a high density. When using a microarray having a biomolecule immobilized thereon at a high density according to an embodiment of the present invention in an analysis, the fluorescence intensity can be increased.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for immobilizing a biomolecule on a solid substrate, comprising:
   coating the solid substrate with silane anhydride such that the silane portion of the silane anhydride is bound to the surface of the solid substrate;
   exposing two carboxyl groups from the anhydride functional group by hydrolysis;
   reacting each exposed carboxyl group with carbodiimide and succinimide to activate the carboxyl group; and
   contacting the biomolecule with the solid substrate having the activated carboxyl groups on its surface such that the biomolecule reacts with an activated carboxyl group derived from the silane anhydride to immobilize the biomolecule on the solid substrate.

2. The method of claim 1, wherein the solid substrate is selected from the group consisting of glass, silicon wafer, polyethylene, polypropylene, polycarbonate, polyester, polyacrylate, and polyurethane.

3. The method of claim 1, wherein the silane anhydride is a compound represented by formula I:

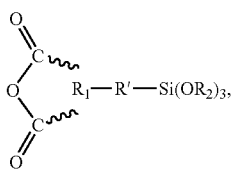

(I)

wherein
$R_1$ is an alkylene group, an arylene group or an alkylarylene group, R' is a substituted or unsubstituted $C_1$–$C_{20}$ alkylene group, a $C_1$–$C_{20}$ arylene group, a $C_1$–$C_{20}$ arylenealkyl group or a $C_1$–$C_{20}$ alkylenearylene group, $R_2$ is a $C_1$–$C_{20}$ alkyl group, an aryl group, an arylenealkyl group, an alkylenearyl group or a hydrogen atom, and the respective $R_2$ groups may be identical to or different from each other.

4. The method of claim 3, wherein $R_1$ is a methyl, ethyl, propyl, or butyl group.

5. The method of claim 3, wherein the silane anhydride is 3-(triethoxysilyl)propylsuccinic anhydride.

6. The method of claim 1, wherein the solid substrate is coated with a solution containing 0.01 to 90% by weight of the silane anhydride.

7. The method of claim 1, wherein the coating the solid substrate with silane anhydride is performed using a method selected from the group consisting of self-assembly molecular coating, spin coating, spraying, and chemical vapor deposition.

8. The method of claim 1, wherein the hydrolysis is performed in an aqueous solution at 20 to 100° C.

9. The method of claim 1, wherein the carbodiimide is 1-ethyl-3-(3-dimethyl-aminopropyl) carbodiimide hydrochloride (EDC) or N,N'-dicyclohexyl carbodiimide (DCC).

10. The method of claim 1, wherein the succinimide is N-hydroxysuccinimide or N-hydroxysulfosuccinimide.

11. The method of claim 1, wherein the carbodiimide or the succinimide is reacted at a concentration of 20 to 200 mM.

12. The method of claim 1, wherein the biomolecule has an amino group.

13. The method of claim 12, wherein the biomolecule is DNA, RNA, PNA, or a protein.

14. The method of claim 1, wherein in coating the solid substrate with silane anhydride, the solid substrate is coated with a silane anhydride solution further comprising 1,2-bis (triethoxysilyl)ethane.

* * * * *

SEQUENCE LISTING

```
<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: probe oligonucleotide

<400> SEQUENCE: 1
caggtgggac tggtt                                                    15
```